US009482639B2

(12) United States Patent
Roundhill (10) Patent No.: US 9,482,639 B2
(45) Date of Patent: Nov. 1, 2016

(54) DETECTION OF VOLATILE CHEMICALS USING AN RFID SENSING SYSTEM (71) Applicant: Empire Technology Development LLC, Wilmington, DE (US)

(72) Inventor: David Max Roundhill, Seattle, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/768,532

(22) PCT Filed: Mar. 11, 2013

(86) PCT No.: PCT/US2013/030144
§ 371 (c)(1),
(2) Date: Aug. 18, 2015

(87) PCT Pub. No.: WO2014/142785
PCT Pub. Date: Sep. 18, 2014

(65) Prior Publication Data
US 2016/0003769 A1 Jan. 7, 2016

(51) Int. Cl.
G01N 33/00 (2006.01)
G01N 27/416 (2006.01)
G01N 27/12 (2006.01)
G01N 27/02 (2006.01)

(52) U.S. Cl.
CPC .......... *G01N 27/416* (2013.01); *G01N 27/025* (2013.01); *G01N 27/122* (2013.01); *G01N 33/0075* (2013.01); *G01N 33/0042* (2013.01); *G01N 33/0044* (2013.01)

(58) Field of Classification Search
CPC ... G01N 27/416; G01N 27/122; G01N 33/42
See application file for complete search history.

(56) References Cited

U.S. PATENT DOCUMENTS 5,120,648 A 6/1992 Lim et al.
5,756,879 A 5/1998 Yamagishi et al.
(Continued)

FOREIGN PATENT DOCUMENTS

WO 2008067244 A2 6/2008

OTHER PUBLICATIONS

"Gold Nanoparticles," American Elements, accessed at http://web.archive.org/web/20130129091951/http://www.americanelements.com/aunp.html, Jan. 2013, 4 Pages.
(Continued)

*Primary Examiner* — Sam P Siefke
(74) *Attorney, Agent, or Firm* — Foley & Lardner LLP (57) ABSTRACT Methods, systems, and apparatuses, including computer programs encoded on computer-readable media, for monitoring volatile chemicals. A system includes an radio-frequency identification (RFID) tag composed of a patterned metal. The patterned metal is configured to absorb a volatile chemical. The RFID tag includes a non-volatile memory configured to store identification data. The RFID tag also includes a receiver that receives a signal at a frequency in a frequency range. The frequency is based upon an amount of the volatile chemical absorbed in the patterned metal. A transmitter of the RFID tag transmits the identification data in response to receiving the signal. The strength of the transmitted identification data is based upon an amount of the absorbed volatile chemical.

15 Claims, 7 Drawing Sheets (56) References Cited

U.S. PATENT DOCUMENTS

| | | |
|---|---|---|
| 2007/0079936 A1 | 4/2007 | Li et al. |
| 2008/0174423 A1 | 7/2008 | Breed |
| 2009/0040044 A1 | 2/2009 | Chiao et al. |
| 2009/0075403 A1 | 3/2009 | Powell et al. |
| 2009/0301382 A1 | 12/2009 | Patel |
| 2010/0024915 A1 | 2/2010 | Thomas et al. |
| 2010/0090802 A1 | 4/2010 | Nilsson et al. |
| 2010/0093096 A1 | 4/2010 | Acharya et al. |
| 2010/0233031 A1 | 9/2010 | Masters |
| 2011/0010107 A1 | 1/2011 | Fedder et al. |
| 2011/0226041 A1 | 9/2011 | Cummins |

OTHER PUBLICATIONS

"Hydrogen Sulfide in Drinking-water," World Health Organization, in Guidelines for drinking-water quality, 2nd ed. vol. 2, pp. 1-9 (1996).
"Material Safety Data Sheet," Sulfur Dioxide—SO2 MSDS, pp. 1-10 (May 20, 1996).
"Model DM-700-SO2 detcon inc. Sulfur Dioxide Sensor," Detcon, accessed at http://www.detcon.com/1-documents/data_sheets/1-sensors/Model%20700/DM-700/Sulfur%20Dioxide%20DM-700-SO2%20PDS.pdf, accessed on Jun. 29, 2015, pp. 1-2.
"Non-line-of-sight propagation," accessed at http://web.archive.org/web/20120923031217/http://en.wikipedia.org/wiki/Non-line-of-sight_propagation, last modified on Aug. 16, 2012, 11 Pages.
"Precious metal Inks," Johnson Matthey Colour Technologies, accessed at http://web.archive.org/web/20130131010822/http://www.glassmatthey.com/products/precious_metals/, Jan. 2013, 1 page.
"Sulfur Dioxide Sensors," Alphasense, Accessed at https://web.archive.org/web/20120624032239/http://www.alphasense.com/alphasense_sensors/sulfur_dioxide_sensors.html, 2009, 1 page.
Espinosa, E., et al., "Drop-coated sensing layers on ultra low power hotplates for an RFID flexible tag microlab," Sensors and Actuators B: Chemical, vol. 144, Issue 2, pp. 462-466 (Feb. 17, 2010).
International Search Report and Written Opinion for International Application No. PCT/US2013/030144 mailed May 21, 2013.
Popa, A., et al., "Which materials block radio waves the most (and why)?," accessed at https://web.archive.org/web/20130211052739/http://www.madsci.org/posts/archives/2002-03/1015162213.Eg.r.html, Feb. 26, 2002, 4 Pages.
Tentzeris, M.M., and Nikolaou, S., "RFID-enabled Ultrasensitive Wireless Sensors Utilizing Inkjet-printed Antennas and Carbon Nanotubes for Gas Detection Applications," IEEE International Conference on Microwaves, Communications, Antennas and Electronics Systems, 2009. COMCAS 2009, pp. 1-5 (Nov. 9-11, 2009).
Wu, O.K.T., and Burns, R.P., "Chemisorption of sulphur dioxide on tungsten and platinum surfaces," Surface and Interface Analysis, vol. 3, Issue 1, pp. 29-33 (Feb. 1981).

DETECTION OF VOLATILE CHEMICALS USING AN RFID SENSING SYSTEM

CROSS-REFERENCE TO RELATED APPLICATION

This application is a U.S. National Stage Application under 35 U.S.C. §371 of International Application Serial No. PCT/US2013/030144, filed on Mar. 11, 2013, the entire disclosure of which is hereby incorporated by reference for all purposes in its entirety.

BACKGROUND

The following description is provided to assist the understanding of the reader. None of the information provided or references cited is admitted to be prior art.

Sulphur compounds and other volatile chemicals can be produced when fossil fuels, such as oil or coal, are burned. Sulphur compounds are a naturally occurring component of fossil fuels. Metal and other inorganic sulphur containing minerals are mined as a by-product of coal. Given the wide range of uses for fossil fuels, monitoring and/or removing sulphur compounds and/or volatile chemicals is useful.

SUMMARY

In general, one aspect of the subject matter described in this specification can be embodied in a system for monitoring volatile chemicals. This includes a radio-frequency identification (RFID) tag composed of a patterned metal. T patterned metal is configured to absorb a volatile chemical. The RFID tag includes a non-volatile memory configured to store identification data. The RFID tag also includes a receiver that receives a signal at a frequency in a frequency range. The frequency is based upon an amount of the volatile chemical absorbed in the patterned metal. A transmitter of the RFID tag transmits the identification data in response to receiving the signal. The strength of the transmitted identification data is based upon an amount of the absorbed volatile chemical.

In one implementation, the system includes an RFID reader that broadcasts a request signal over a plurality of frequencies in the frequency range. A response from the RFID tag is received at a particular request frequency. The strength of the received response is based upon the amount of absorbed volatile chemical. A level of the volatile chemical absorbed in the patterned metal is determined based upon the strength of the received response and the particular request frequency.

In one implementation, one or more of the first plurality of product identifiers comprises barcode information for a product. In another implementation one or more of the first plurality of product identifiers comprises a description of a product or packaging material information for the product.

In another implementation, the system includes a flow tube that is configured to convey a fluid. The flow tube includes a metallic section configured to block the request signal and a non-metallic section configured to allow passage of the request signal. The RFID tag is attached within the flow tube adjacent to the non-metallic window portion.

In another implementation, the system includes a flow tube that is configured to convey a fluid. The flow tube includes an analysis chamber. The RFID tag is mounted within the analysis chamber. A first valve connects the flow tube to the analysis chamber and is configured to allow the fluid to flow from the flow tube into the analysis chamber. A second valve connects the flow tube to the analysis chamber and is configured to allow the fluid to flow from the analysis into the flow tube.

In another implementation, a transmitter broadcasts a request signal over a request frequency range. A first response is received from an RFID tag in response to broadcasting the request signal at a first request frequency within the request frequency range. The RFID tag is comprised of a patterned metal that absorbs a first volatile chemical. The strength of the received first response is based upon an amount of the first volatile chemical absorbed by the patterned metal. A level of the first volatile chemical absorbed in the patterned metal is determined based upon the strength of the received first response and the first request frequency.

Other implementations include corresponding methods, systems, apparatuses, and computer-readable media configured to perform the actions of the various methods.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings. Like reference numbers and designations in the various drawings indicate like elements.

DETAILED DESCRIPTION

Described herein are illustrative methods and apparatuses relating to a remote monitoring system of one or more volatile chemicals. The remote monitoring system includes one or more RFID tags that absorb one or more volatile chemicals. In one implementation, the monitoring of the volatile chemicals can be continuous. In various implementations, the one or more volatile chemicals that can be monitored include, but are not limited to, hydrogen sulphide, dimethyl sulphoxide and its homologues, thiophene and substituted thiophense, sulphur dioxide, thiols, sulphides such as $CH_3$, $C_2H_5$, $C_3H_7$, $C_4H_9$, or any sulphide of general formula RSR', dialkyl selenides, dimethyl selenide and its homologues, other selenium analogs, etc. R and R' can represent an alkane, alkene, or other carbon-containing group of atoms. The RFID tags can be made of a substance that absorbs one or more of the volatile chemicals. The RFID tags can be made of gold, silver, platinum, tungsten, rhodium, iridium, ruthenium, osmium, palladium, cadmium, etc. The choice of the material for the RFID tags can be based upon how that material absorbs a volatile chemical that is to be monitored. For example, gold RFID tags can be used to monitor hydrogen sulphide or other organic sulphur compounds. As another non-limiting example, platinum or tungsten RFID tags can be used to monitor sulphur dioxide. An RFID reader can be used to broadcast a signal to one or more RFID tags at a specific frequency or over a frequency range. An RFID tag that receives the RFID reader's signal can respond with data, such as identification data. The power of the signal transmitted from the RFID tag to the RFID reader can be reduced based upon the amount of volatile chemical absorbed by the RFID tag. The RFID reader can use the power of the received signal to determine how much of the volatile chemical the RFID tag absorbed. In another implementation, the radio frequency of the received signal can also be used to determine how much of the volatile chemical the RFID tag absorbed. In yet another implementation, the frequency at which the RFID tag responds is influenced by the amount of volatile chemical absorbed by the RFID tag. In this implementation, the RFID reader can broadcast its signal over a frequency range over a period of time. The frequency at which the RFID tag responds can be used to determine the amount of volatile chemical absorbed by the RFID tag.

Figure 1:
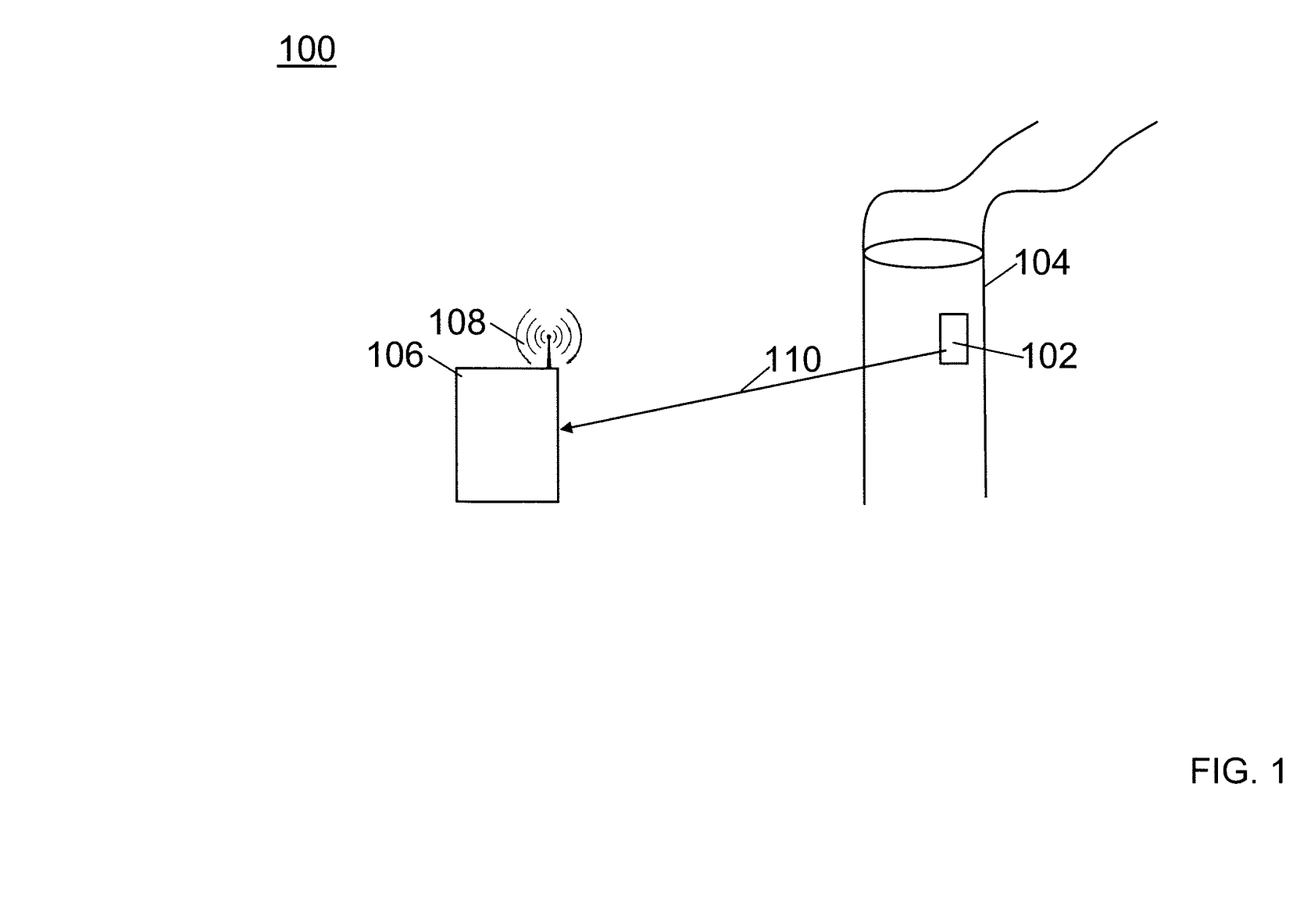
FIG. 1 illustrates a volatile chemicals monitoring system in accordance with an illustrative embodiment.

FIG. 1 illustrates a volatile chemical monitoring system 100 in accordance with an illustrative embodiment. The volatile chemical monitoring system 100 includes an RFID tag 102. While only a single RFID tag 102 is illustrated in FIG. 1, multiple RFID tags can be monitored by the volatile chemical monitoring system 100. The RFID tag 102 can be a passive tag that does not include a battery. The passive tag receives power from the electromagnetic field generated by receiving a signal from an RFID reader 106. The RFID tag 102 can also be an active tag that includes a battery that provides power to the RFID tag 102. The RFID tag 102 can be placed in the path a fluid flowing through a tube 104. The RFID reader 106 can broadcast a signal using a transmitter 108 which can be detected by the RFID tag 102. In response, the RFID tag 102 can respond 110 with data, such as, but not limited to, an identifier of the RFID tag, a location, an identifier of the tube 104, etc.

Figure 2:
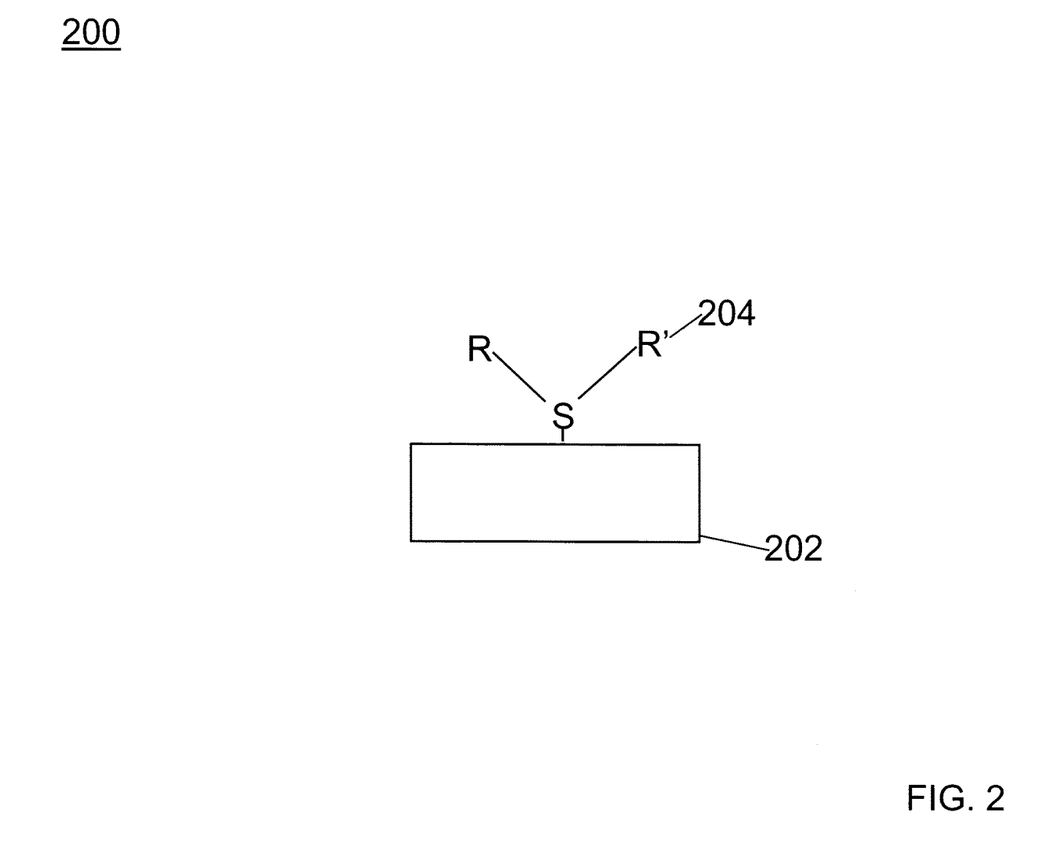
FIG. 2 illustrates a radio-frequency identification (RFID) tag in accordance with an illustrative embodiment.

FIG. 2 illustrates a radio-frequency identification (RFID) tag 202 in accordance with an illustrative embodiment. The RFID tag 202 can be designed to absorb particular volatile chemicals, such as sulphides 204 that have the general formula RSR'. To absorb sulphides 204, the RFID tag 202 can be composed of a material that is a strong absorbent for organic sulphur compounds, such as, but not limited to, gold, silver, noble metals, etc. Sulphides 204 can bind with the RFID tag 202 through at least the sulphur atoms of the sulphide 204.

In other implementations, the RFID tag can be made of a material that is a strong absorbent for sulphur dioxide, such as, but not limited to, platinum, tungsten, etc. Platinum has a strong affinity for sulphur as evidenced by the very low solubility of platinum sulphide and by its use as a catalyst for the oxidation of sulphur dioxide to sulphur trioxide with air. Tungsten can be used in the RFID tag since tungsten can form numerous strongly bonded tungsten sulphides. Both platinum and tungsten strongly chemisorb sulphur dioxide onto their surface. In addition to platinum and tungsten, other soft polarizable metals can be used in the RFID tag.

Sulphur dioxide can bind to the material of the RFID tag through sulphur, oxygen, or both atoms. The bonding mode can be predicted based on the hard and soft acid-base concept. Hard non-polarizable atoms preferentially bind to each other as do soft polarizable atoms. Oxygen is a hard non-polarizable atom and sulfur is a soft polarizable atom. Since sulphur is less prevalent in emission gases than oxygen, an RFID tag with platinum or tungsten will target binding the sulphur atom in sulphur dioxide.

The absorbed volatile chemical occurs at least on portions of the RFID tag that receives the radio signal from an RFID reader. The portions can be a patterned metal made by printing and curing a metallic ink. There may be advantages in patterning the metal RFID by printing it with a metallic ink followed by sintering. The approach creates an uneven metallic surface that retains the high resistivity of the metal RFID by leaves a surface with more absorption area and adherence sites for the volatile chemical. The absorbed volatile chemical can also occur on portions of the RFID tag that transmit a radio signal to the RFID reader. Accordingly, the intensity and wavelength of the radio signal received by the RFID tag, as well as, the radio signal transmitted by the RFID tag is affected by the amount of the volatile chemical absorbed by the RFID tag.

An RFID tag can be made through various processes. In one implementation, an RFID tag can be printed onto a flexible substrate such as polyimide kapton or polyester mylar. The printing can be done using an ink or paste that includes the appropriate material that will absorb the desired volatile chemical. For example, the ink can include gold, silver, platinum, tungsten, etc. In another implementation, nanoparticles of the selected material can be used to formulate the ink or paste. The RFID tag can be printed on a substrate as a pattern. The printed metal pattern can then be thermally cured. The RFID tag is thus composed of a patterned metal.

Figure 3:
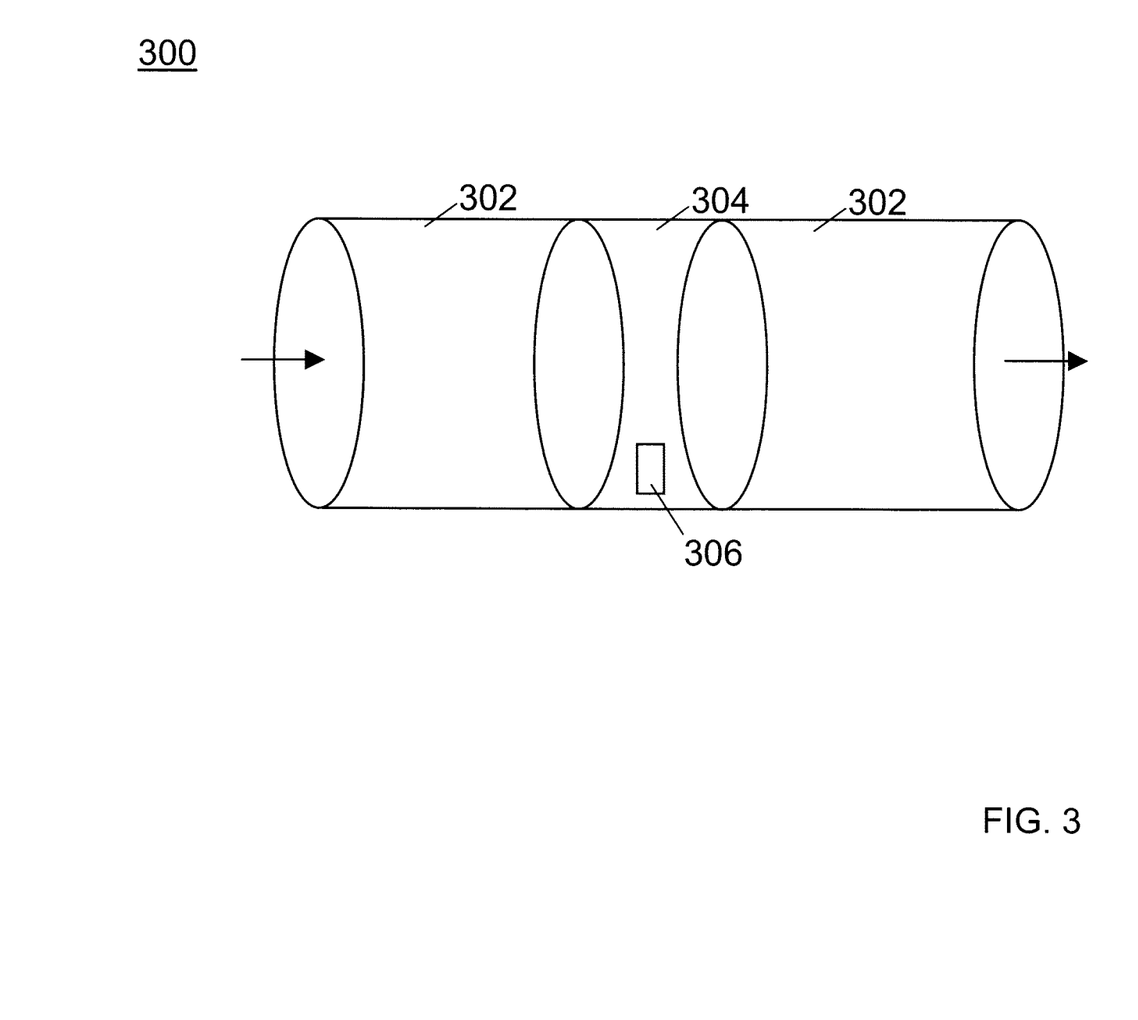
FIG. 3 illustrates a portion of a flow tube with an inline RFID tag in accordance with an illustrative embodiment.

When the RFID tag is printed onto a flexible substrate, the RFID tag is flexible enough to be fitted into various existing components. For example, an RFID tag can be inserted into a flow tube that exposes the RFID tag to a flowing fluid, while still allowing the fluid to flow through the flow tube. In one implementation, the flow tube can be made of material that is transparent to radio waves, such as a synthetic polymer. Existing metal tubes, which can be non-transparent to radio waves, can also be equipped with RFID tags. For example, the flow tube 300 can include metallic portions 302 that are made of metal or other materials, which prohibit the passing of radio signals from an RFID reader. Accordingly, the RFID tag 306 can be placed in a non-metallic portion 304, that allows the RFID tag to be interrogated from outside of the flow tube 300. The non-metallic portion 304 can be made of a dielectric or a synthetic polymer. In one implementation, the RFID tag can be placed at the top of the flow tube without requiring a non-metallic portion. In other implementations, the RFID tag can be placed in the interior of the flow tube if a synthetic polymer portion is inserted into the metal flow tube. FIG. 3 illustrates a portion of a flow tube 300 with an inline RFID tag 306 in accordance with an illustrative embodiment. The flow tube 300 can be a flue for exhaust. For example, the flow tube 300 can move flue gases from power plants, home heating units, gas pipelines, or tailpipes of vehicles. As a non-limiting example, the flow tube can be a flow tube for emissions from burning natural gas.

Figure 4:
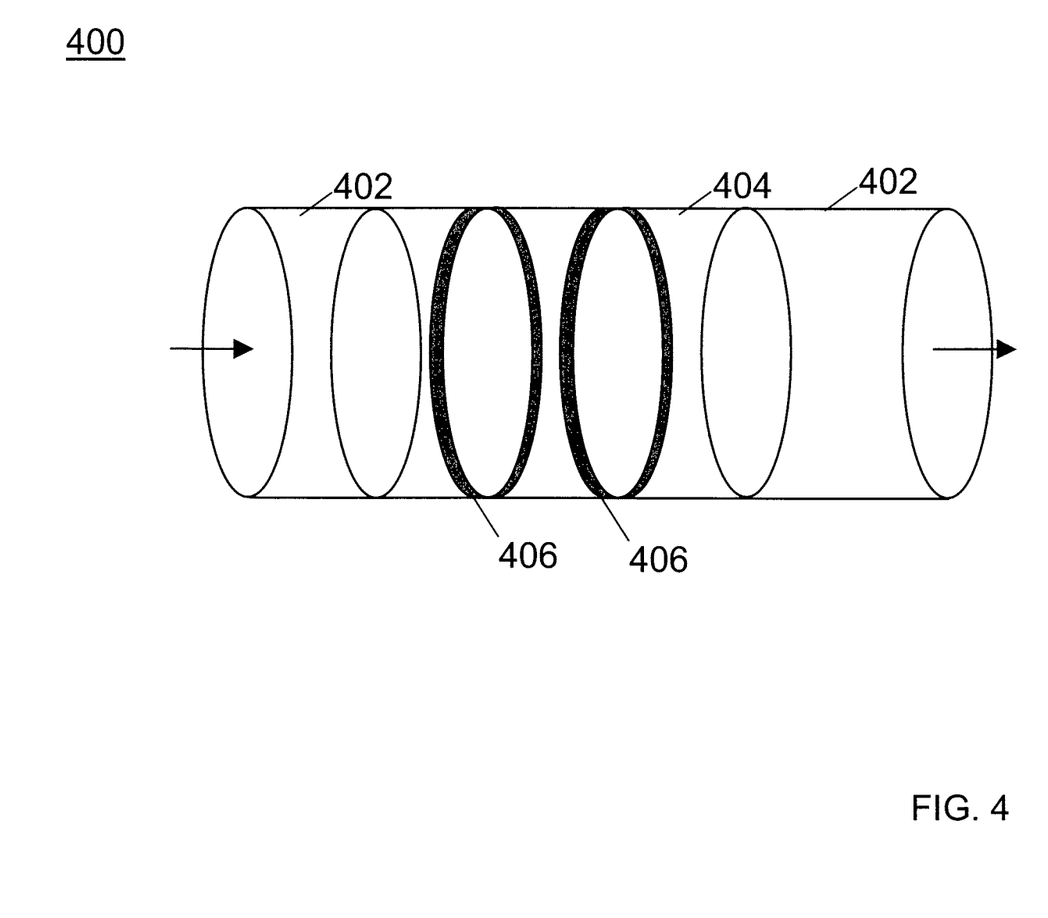
FIG. 4 illustrates a portion of a flow tube with inline RFID tags in accordance with an illustrative embodiment.

FIG. 4 illustrates a portion of a flow tube 400 with inline RFID tags 406 in accordance with another illustrative embodiment. In this illustrated example, RFID tags 406 can be made to fit the inner diameter of the flow tube 400. The RFID tags 406 are, therefore, exposed to a gas as the gas moves through the flow tube 400. Similar to FIG. 3, the RFID tags 406 are located in a non-metallic portion 404, that allows the RFID tag to be interrogated from outside of the flow tube 400. The flow tube 400 can also include metallic portions 402, which can inhibit the RFID reader's transmissions.

Figure 5:
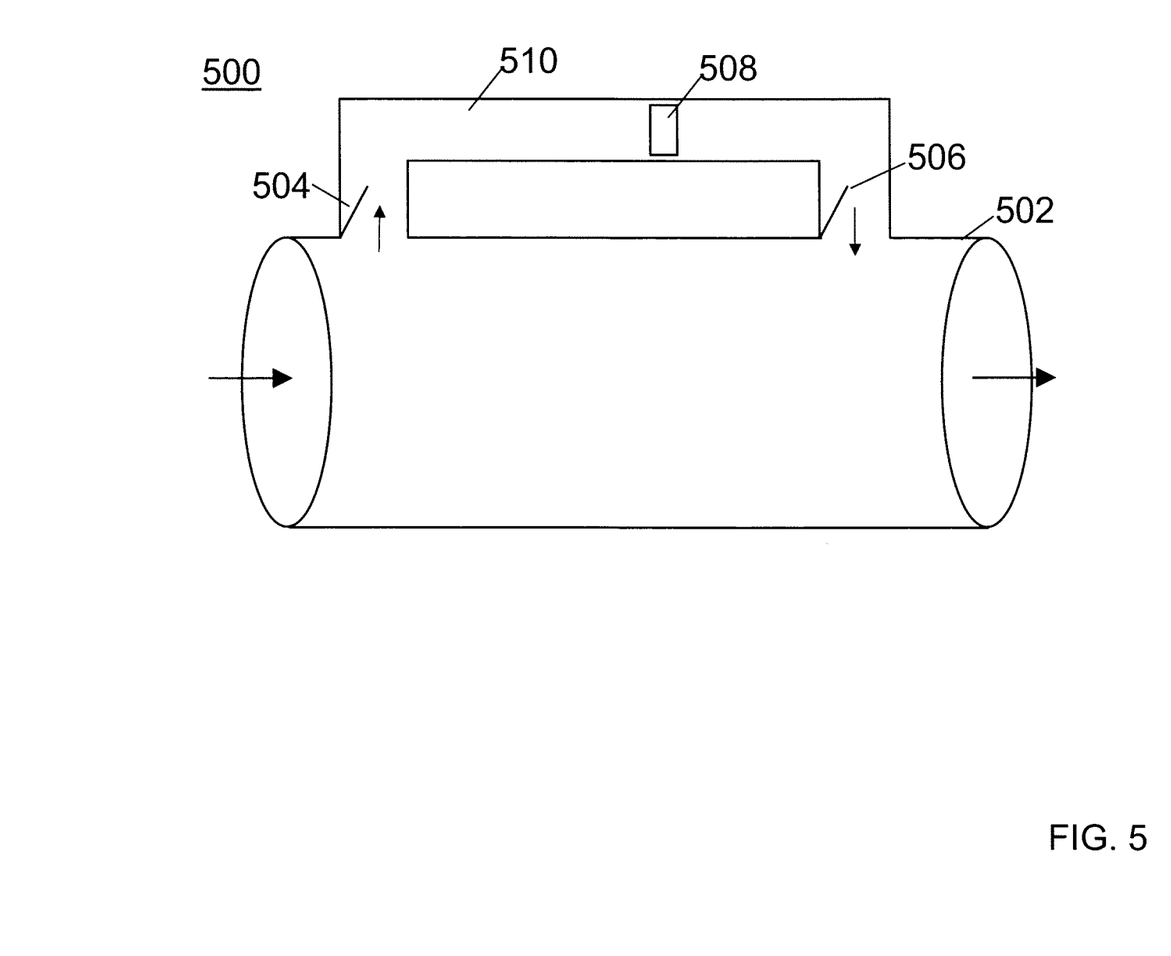
FIG. 5 illustrates a portion of a tube with an analysis chamber that includes an RFID tag in accordance with an illustrative embodiment.

In another implementation, an analysis chamber can be used. In this implementation, an RFID tag can be used in a metal flow tube that does not require major modification to the integrity of the metal flow tube. FIG. 5 illustrates a portion of a flow tube 502 with an analysis chamber 510 that includes an RFID tag 508 in accordance with an illustrative embodiment. The RFID tag 508 can be placed in parallel with the flowing gas in the flow tube 502 inside the analysis chamber 510. The RFID tag 508, however, is not included inline within the flow tube 502. In this implementation, the flow tube 502 can be comprised of a metal and the analysis chamber 510 can be made of a material that is transparent to radio waves. The analysis chamber 510 is connected to the flow tube 502 through two valves 504 and 506. The valves 504 and 506 can be opened when an analytical sample is needed. The opening and closing of the valves 504 and 506 can be timed to correspond with the reading of the RFID tag 508 or the usage of the flow tube 502. For example, the valves 504 and 506 can be opened when there is a fluid flowing through the flow tube 502. In another implementation, the valves 504 and 506 can be opened some amount of time, e.g., 5 minutes, 30 minutes, 60 minutes, prior to the reading of the RFID tag 508. In yet another implementation, the valves 504 and 506 can be opened on a predetermined schedule. The valves 504 and 506 can also be controlled by the RFID tag. For example, the RFID tag can control the opening and closing of the valves 504 and 506 based upon receiving signals from an RFID reader. For example, the RFID tag can open the valves 504 and 506 when a first signal is received. When the RFID tag receives another signal, the valves 504 and 506 can be closed. In one example, the RFID tag can include a battery that provides power to components that open and close the valves 504 and 506. A gas flushing loop can be incorporated into the opening and closing of the valves 504 and 506 to flush the analyte gases out of the analysis chamber 510. For example, the opening and closing of the valves 504 and 506 can be sequenced, such that the valves 504 and 506 are opened, the RFID tag 508 is read, and then the analyte gases can be flushed from the analysis chamber 510.

The RFID tags described above can be used to continually monitor volatile chemicals in a flowing gas. As the monitored volatile chemical is absorbed into the RFID tag, the characteristics of the RFID tag change. For example, the frequency at which an RFID tag responds can change based upon the amount of volatile chemical absorbed by the RFID tag. An RFID reader can broadcast a signal over a frequency range and determine at which frequency the RFID tag responds. If different volatile chemicals have their maximum radio-frequency absorption in different wavelength ranges, an RFID reader can selectively detect each of the volatile chemicals by using read frequency ranges specific to the wavelength ranges of the volatile chemicals. Empirical data can be used to map a response frequency to an amount of volatile chemical absorbed. For example, a clean RFID tag can be used to determine a base frequency that signifies that the RFID tag has not absorbed a detectable amount of the volatile chemical. RFID tags can then be coated with volatile chemicals that are to be monitored. The response radio frequency of each coated RFID tag can then be determined by an RFID reader broadcasting over a frequency range and noting when a particular RFID tag responds. The amount of volatile chemical absorbed by the RFID tag can also impact the strength of the signal transmitted by the RFID tag. The impact on the strength of the signal based upon the amount of volatile chemical absorbed can also be determined empirically. The amount of volatile chemical absorbed by the RFID tag can also impact the strength of the signal received by the RFID tag. The impact on the strength of the signal based upon the amount of volatile chemical absorbed can also be determined empirically. An RFID reader can broadcast a signal over a power range. For example, the RFID reader can start broadcasting the signal with increasing power. The power at which the RFID tag responds can be used to determine the amount of volatile chemical absorbed by the RFID tag. Alternatively, the RFID reader can broadcast the signal over a decreasing power range. The last power at which the RFID tag responds can be used to determine the amount of volatile chemical absorbed by the RFID tag. Background readings can be taken to confirm if there are interferences from hydrocarbons or other components that are not desired to be monitored.

A monitoring system can be constructed using one or more RFID tags and at least one RFID reader. The RFID tags can be placed in various locations, such as in or near flow tubes. As gases pass over the RFID tags, the RFID tags absorb one or more volatile chemicals. The volatile chemical absorbed is based upon the material of the RFID tag. The RFID reader can then broadcast a radio signal to the RFID tags. Responses from the RFID tags can be used to determine how much of the respective volatile chemical each RFID tag has absorbed.

Figure 6:
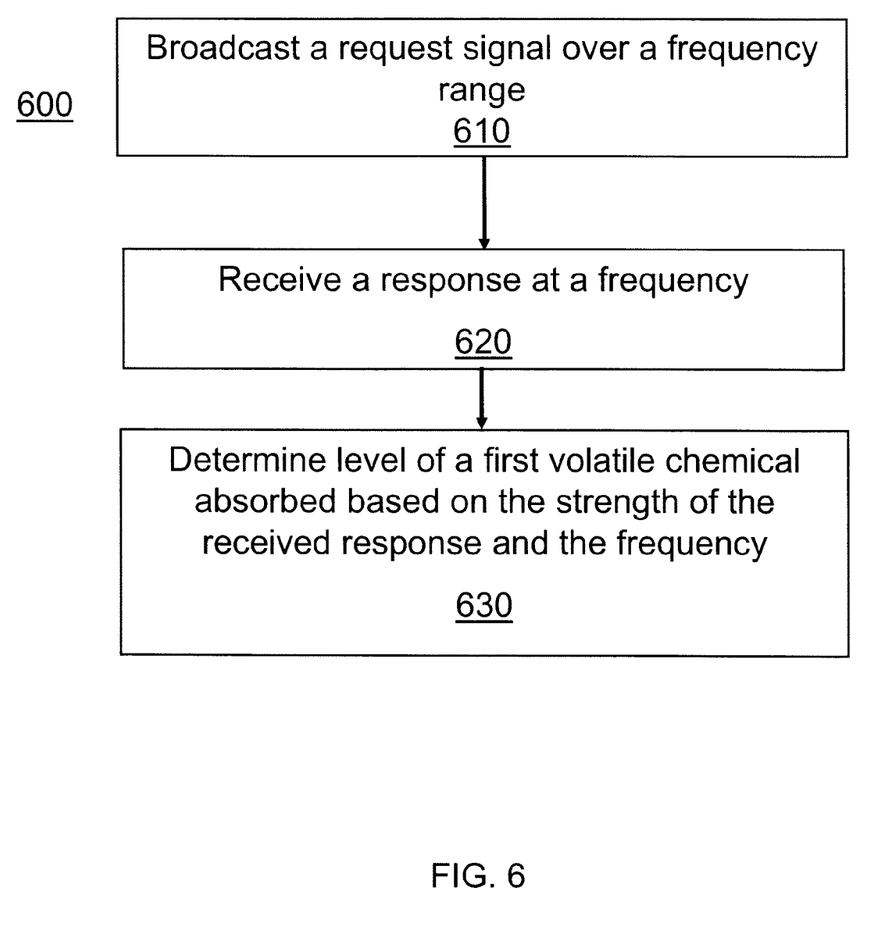
FIG. 6 is a flow diagram of a procedure for determining an absorbed level of a volatile chemical in accordance with an illustrative embodiment.

FIG. 6 is a flow diagram of a procedure 600 for determining an absorbed level of a volatile chemical in accordance with an illustrative embodiment. Additional, fewer, or different operations of the procedure 600 may be performed, depending on the particular embodiment. The procedure 600 can be implemented on a computing device. In one implementation, the procedure 600 is encoded on a computer-readable medium that contains instructions that, when executed by a computing device, cause the computing device to perform operations of the procedure 600.

An RFID reader can broadcast a request signal over a frequency range to one or more RFID tags (610). For example, an RFID reader that is monitoring a particular volatile chemical, such as hydrogen sulphide, can broadcast the request signal over a frequency range associated with hydrogen sulphide. The frequency range associated with hydrogen sulphide can be determined empirically, as described in greater detail above. The frequency range is wide enough to cover when the RFID tag has not absorbed any of the volatile chemical and when the RFID tag has absorbed a maximum amount of the volatile chemical. The RFID reader receives a response from an RFID tag at a frequency (620). The response can include information that can identify the particular RFID tag or a location of the RFID tag. The strength of the received signal as well as the received frequency can be used to determine the amount of volatile chemical that the RFID tag has absorbed (630). In other implementations, using only the received frequency or received signal strength can be used to determine the amount of volatile chemical that the RFID tag has absorbed. Determining the amount of volatile chemical absorbed by the RFID tag can be used to monitor changes in concentration of the volatile chemical in the gas that flows over the RFID tag.

Figure 7:
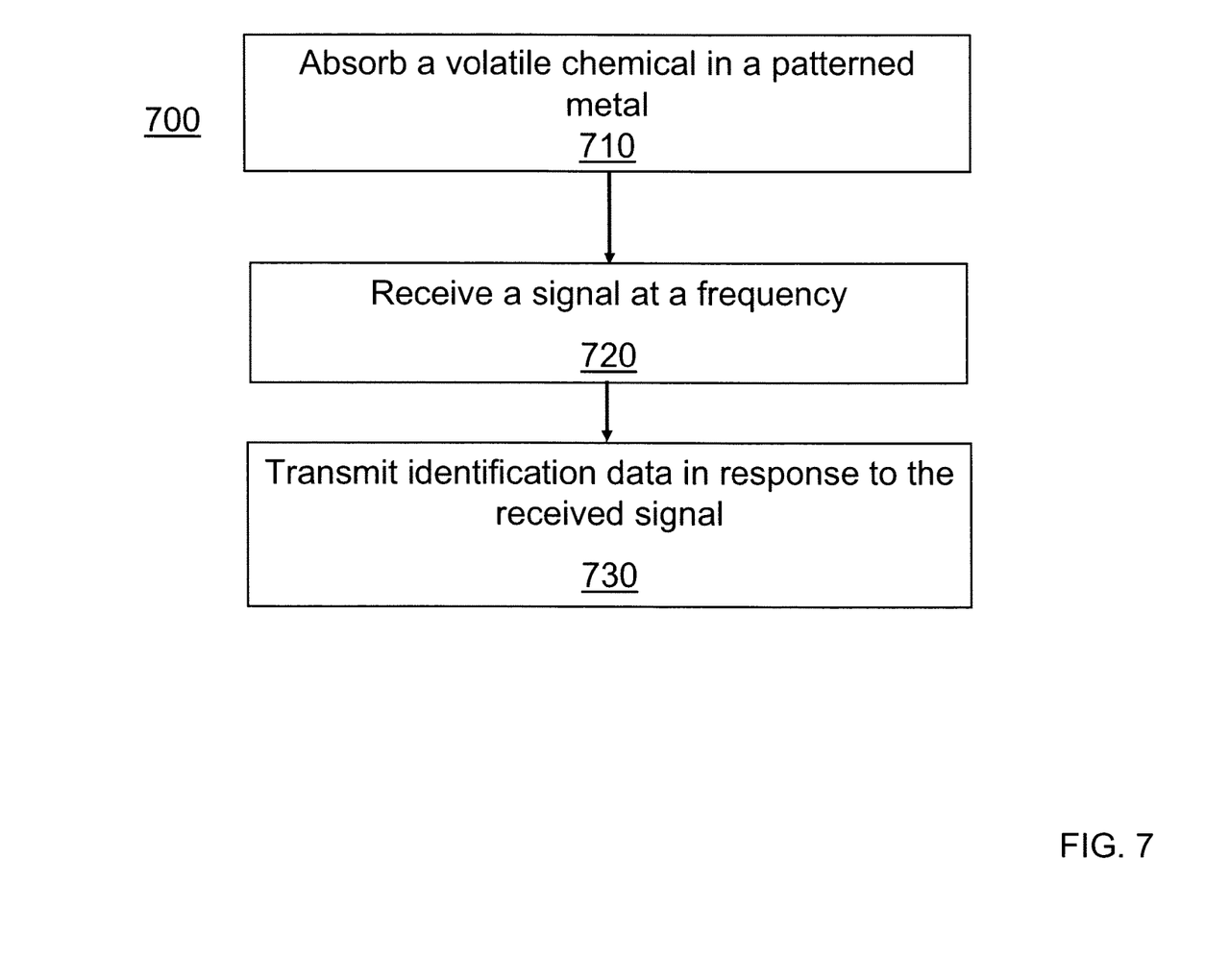
FIG. 7 is a flow diagram of a procedure for transmitting a signal indicating an absorbed level of a volatile chemical in accordance with an illustrative embodiment.

FIG. 7 is a flow diagram of a procedure 700 for transmitting a signal indicating an absorbed level of a volatile chemical in accordance with an illustrative embodiment. Additional, fewer, or different operations of the procedure 700 may be performed, depending on the particular embodiment. Once placed in its desired location, a patterned metal of an RFID tag absorbs a volatile chemical (710). The RFID tag receives a signal at the response frequency of the RFID tag (720). For example, the received signal can be from an RFID reader. The response frequency of the RFID tag is dependent on the amount of volatile chemical absorbed by the RFID tag. Accordingly, the response frequency for an RFID tag will change as the RFID tag absorbs more of the volatile chemical. Based upon receiving the signal at the response frequency, the RFID tag transmits identification data (730). In one implementation, the RFID tag transmits at a constant power. The absorbed volatile chemical, however, can absorb a portion of the transmitted signal, thereby, lowering its power. The RFID tag can power its transmitter using a battery or through the energy provided by receiving the signal at the response frequency. As described in greater detail above, the RFID reader can determine the amount of volatile chemical absorbed by the RFID tag based upon the frequency at which the RFID tag responded and/or by the strength of the signal received by the RFID reader.

EXAMPLES

The present systems and methods will be understood more readily by reference to the following example, which is provided by way of illustration and is not intended to be limiting in any way.

Example 1

Methanethiol Example

An RFID tag can be configured to absorbed methanethiol. As the RFID tag absorbs methanethiol, the intensity of a signal received by the RFID tag and also the intensity of a signal transmitted from the RFID tag will change based upon one or more factors. For example, the absorption of the organic sulfur compound at the chosen microwave frequency, which will depend on the molar absorptivity $\epsilon$ of the organic sulfur compound at that frequency, can affect the intensity of signals. A second factor is the thickness of the adsorbed layers of the organic sulfur compound on the surface of the RFID tag. The absorption of the microwave radiation (electromagnetic radiation) is expected to follow the Beer-Lambert (Beer's) Law, namely $A=\epsilon c l$ where, for the organic sulfur compound, A is the absorbance, $\epsilon$ is the molar absorptivity in $l \cdot mol^{-1} \cdot cm^{-1}$, c is the concentration in moles per liter, and l is the path length (thickness) expressed in cm. Molar absorptivities $\epsilon$ can range from 5 to 2,000.

Taking methanethiol ($CH_3SH$) with a molecular weight of 48 as an example; pure methanethiol that has a density of approximately 0.9 $g \cdot cm^{-3}$ absorbed onto the surface of an RFID will have a concentration c of 18.75 moles $liter^{-1}$. Assuming a molar absorptivity $\epsilon$ of $5 \times 10^2$ $l \cdot mol^{-1} \cdot cm^{-1}$ and a layer thickness of methanethiol on the RFID surface of 100 molecules, the path length l will be approximately $2 \times 5 \times 10^{-6}$ cm if a single molecular layer of methanethiol has a thickness of 500 picometers (pm). The factor of 2 results from the incident radiation beam passing through a 500 picometer thickness of methanethiol as it transmits through the methanethiol layer for passage both to and from the surface of the RFID tag. Applying Beer's Law gives:

$$A=(5 \times 10^2) \times 18.75 \times (10 \times 10^{-6})=93.75 \times 10^{-3} \text{ or } 0.09375$$

The absorbance A is defined by equation $A=-\log I/I_o$ where I is the transmitted intensity after passage through the methanethiol layer and $I_o$ is the incident (initial) intensity, or the intensity from a clean RFID tag. The ratio $I/I_0$ is therefore the transmittance.

In one implementation, the system is designed for the absorbance A to be within the range of >0 to 2, because the transmittance needs to be within a measurable range. If the transmittance is too high the intensity of the radiation I will be within statistical error of the initial $I_0$ value, whereas if the transmittance is too low the intensity of the radiation I will be too low to get a measurable value above the baseline value of the instrument. The following examples show these trends:

For $A=4 \times 10^{-3}$, 0.3 and 2, the transmittance $I/I_o$ is 0.99 (99%), 0.5 (50%) and 0.01 (1%), respectively.

Implementations of portions of the subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

One or more flow diagrams have been used herein. The use of flow diagrams is not meant to be limiting with respect to the order of operations performed. The herein-described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality, and any two components capable of being so associated can also be viewed as being "operably couplable" to each other to achieve the desired functionality. Specific examples of "operably couplable" include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system for detecting a volatile chemical, the system comprising:
    a radio-frequency identification (RFID) tag composed of a patterned metal, wherein the patterned metal is configured to absorb a volatile chemical, and wherein the RFID tag comprises:
        non-volatile memory configured to:
            store identification data;
        a receiver configured to:
            receive a signal at a frequency in a frequency range, wherein the frequency is based upon an amount of the volatile chemical absorbed in the patterned metal;
        a transmitter configured to:
            transmit the identification data in response to receiving the signal, wherein a strength of the transmitted identification data is based upon an amount of the absorbed volatile chemical; and
    an RFID reader configured to:
        broadcast a request signal over a plurality of frequencies in the frequency range;
        receive a response from the RFID tag at a particular request frequency, wherein a strength of the received response is based upon the amount of absorbed volatile chemical; and
        determine a level of the volatile chemical absorbed in the patterned metal based upon the strength of the received response and the particular request frequency; and
    a flow tube configured to convey a fluid, wherein the flow tube is configured to block the request signal;
    an analysis chamber, wherein the RFID tag is mounted within the analysis chamber;
    a first valve connecting the flow tube and the analysis chamber and configured to allow the fluid to flow from the flow tube into the analysis chamber; and
    a second valve connecting the flow tube and the analysis chamber and configured to allow the fluid to flow from the analysis chamber into the flow chamber.

2. The system of claim 1, wherein the patterned metal is configured to absorb the volatile chemical from a fluid.

3. The system of claim 1, wherein a strength of the received signal is based upon the amount of the volatile chemical absorbed in the patterned metal.

4. The system of claim 1,
    wherein the flow tube further comprises:
        a non-metallic window portion, wherein the RFID tag is attached within the flow tube adjacent to the non-metallic window portion, and wherein the non-metallic window is configured to allow passage of the request signal.

5. The system of claim 4, wherein the non-metallic window portion is comprised of polytetraflouroethylene.

6. The system of claim 1, wherein the RFID tag is configured to control the opening and closing of the first valve and the second valve based upon the received signal.

7. The system of claim 1, further comprising a flexible substrate, wherein the RFID tag is attached to the flexible substrate.

8. The system of claim 7, wherein the flexible substrate comprises one of a polyimide film and a biaxially-oriented polyethylene terephthalate.

9. The system of claim 1, wherein the patterned metal comprises gold or silver.

10. The system of claim 9, wherein the volatile chemical is one of a sulfide or a thiol.

11. The system of claim 1, wherein the patterned metal comprises platinum or tungsten.

12. The system of claim 10, wherein the volatile chemical is sulphur dioxide.

13. A sensor for detecting a volatile chemical, the sensor comprising:
    a chamber comprising a polymer section configured to flow a fluid;
    a substrate attached onto an inner wall of the polymer section of the chamber;
    a radio-frequency identification (RFID) tag formed on a surface of the substrate, wherein the RFID tag is composed of a patterned metal configured to absorb a volatile chemical, the RFID tag comprising:
    non-volatile memory configured to store identification data;
    a receiver configured to receive a signal at a frequency in a frequency range, wherein the frequency is based upon an amount of the volatile chemical absorbed in the patterned metal; and
    a transmitter configured to transmit the identification data in response to receiving the signal, wherein a strength of the transmitted identification data is based upon the amount of the volatile chemical absorbed in the patterned metal; and
    an RFID reader configured to:
    broadcast a request signal over a plurality of frequencies in a request frequency range;
    receive a response from the RFID tag at a particular request frequency; and determine a level of the volatile chemical absorbed in the patterned metal based upon a strength of the received response from the RFID tag and the particular request frequency a flow tube configured to convey a fluid, wherein the flow tube is configured to block the request signal;

an analysis chamber, wherein the RFID tag is mounted within the analysis chamber;

a first valve connecting the flow tube and the analysis chamber and configured to allow the fluid to flow from the flow tube into the analysis chamber; and a second valve connecting the flow tube and the analysis chamber and configured to allow the fluid to flow from the analysis chamber into the flow chamber.

14. The sensor of claim 13, wherein the patterned metal is configured to absorb the volatile chemical from the fluid.

15. The sensor of claim 13, wherein a strength of the signal is based upon the amount of the volatile chemical absorbed in the patterned metal.

* * * * *